United States Patent [19]
LaBash

[11] Patent Number: 5,499,989
[45] Date of Patent: Mar. 19, 1996

[54] BREAST BIOPSY APPARATUS AND METHOD OF USE

[76] Inventor: Stephen S. LaBash, 902 W. Columbia Blvd., Oberlin, Kans. 67749

[21] Appl. No.: 300,650

[22] Filed: Dec. 22, 1994

[51] Int. Cl.⁶ .................................................. A61B 19/00
[52] U.S. Cl. .......................................... 606/130; 128/754
[58] Field of Search ........................ 128/749, 751–754, 128/653.1; 606/130, 167, 170, 172, 180, 184, 185; 604/115–117, 180

[56] References Cited

U.S. PATENT DOCUMENTS

| | | | |
|---|---|---|---|
| 4,580,561 | 4/1986 | Williamson | 606/130 |
| 4,691,333 | 9/1987 | Gabriele et al. | 128/754 |
| 4,798,212 | 1/1989 | Arane | 128/749 |
| 4,915,694 | 4/1990 | Yamamoto et al. | 604/180 |
| 5,056,523 | 10/1991 | Hotchkiss et al. | 606/130 |
| 5,078,142 | 1/1992 | Siczek et al. | 128/754 |
| 5,111,828 | 5/1992 | Kornbey et al. | 128/754 |
| 5,197,482 | 3/1993 | Rank et al. | 606/116 |
| 5,209,232 | 5/1993 | Levene | 128/653.1 |
| 5,213,100 | 5/1993 | Summ | 606/130 |

Primary Examiner—Max Hindenburg
Attorney, Agent, or Firm—Michael I. Kroll

[57] ABSTRACT

An apparatus and method for obtaining samples of suspicious breast tissue is disclosed. The breast is placed between two plates, which compress, and therefore stabilize the tissue. The upper compression plate has an aperture therein that allows for the placement of a guide spool having a flesh adhering surface thereon onto the compressed breast itself. Markings on the spool allow for accurate placement using the cross hairs, or laser light pointer, of the mammographic unit. For additional placement verification, the guide spool is radiopaque and, thus, an X-ray taken directly down through the aperture will aid in ascertaining if the spool is properly placed. A tubular punch is advanced and rotated, cutting through the tissue, which is recovered in the tube. Alternatively, a localizing needle can be placed with its tip proximate the calcification, a guide wire mandrel having the same diameter as the guide spool aperture placed over it, the guide spool placed and aligned, the mandrel removed, and the tubular punch is inserted and advanced as above, removing the tissue in question, along with the localizing needle.

3 Claims, 3 Drawing Sheets

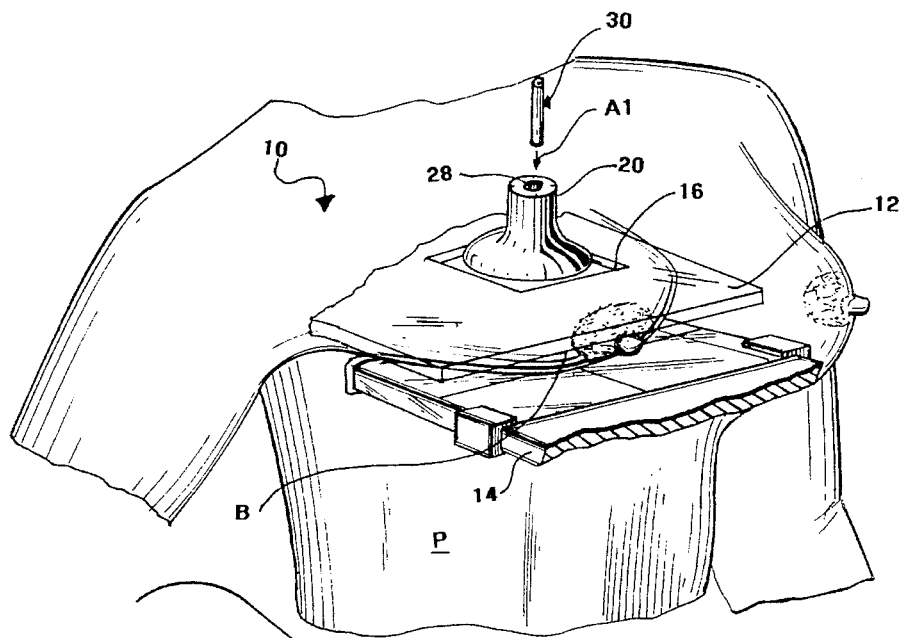
Fig. 1
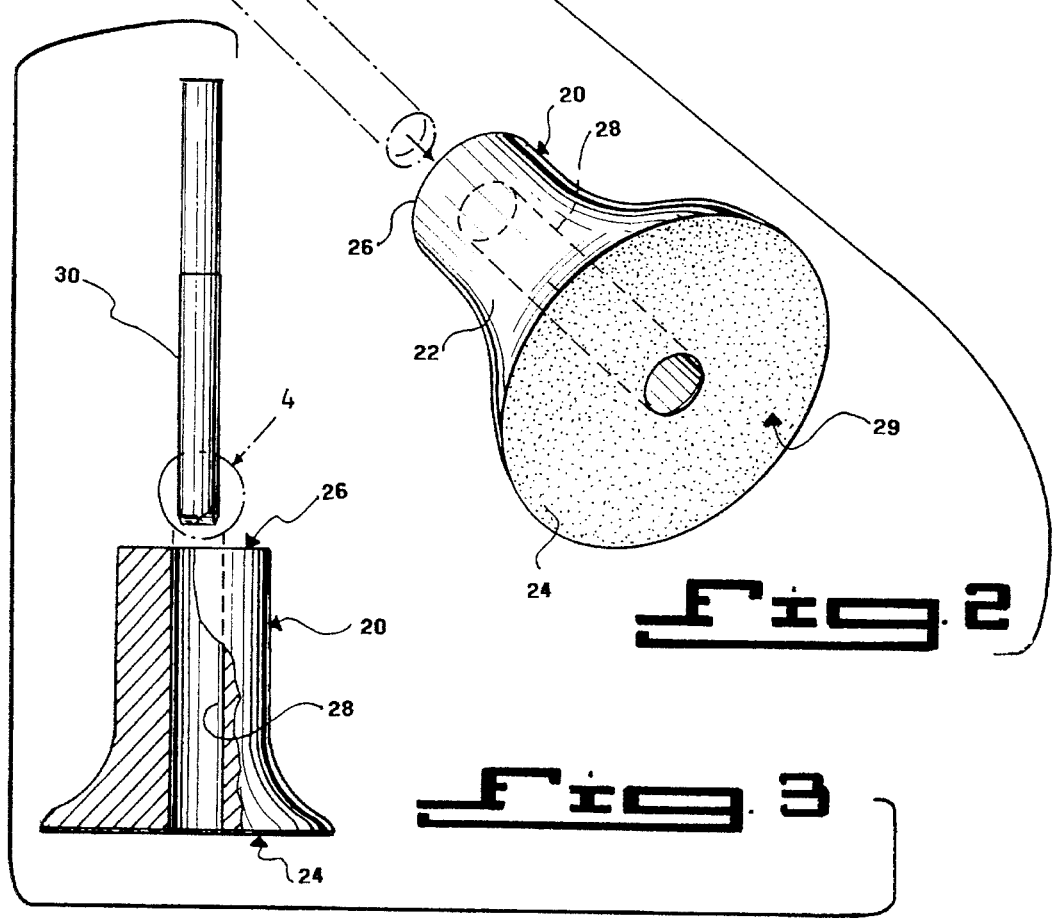
Fig. 2
Fig. 3

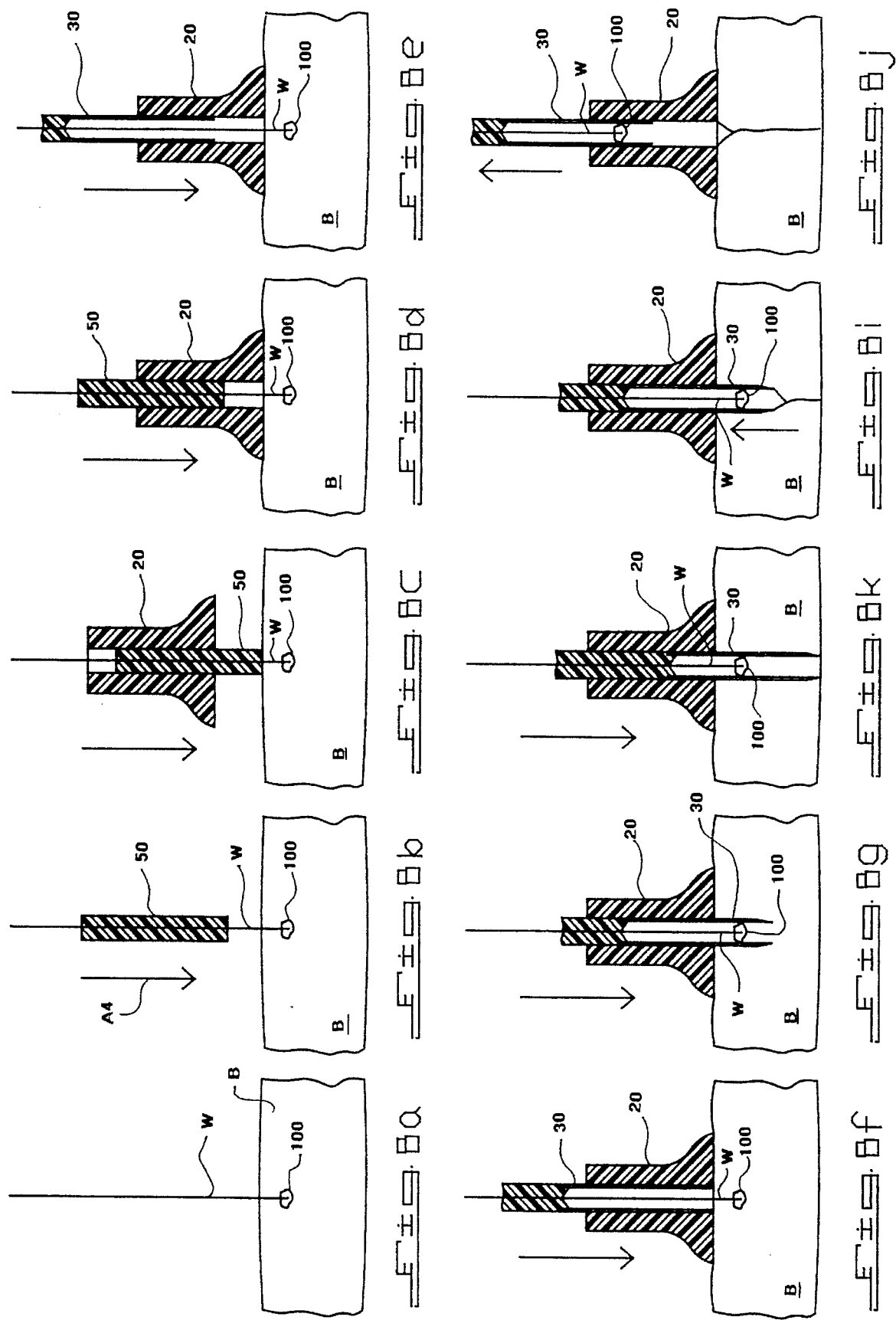

BREAST BIOPSY APPARATUS AND METHOD OF USE

BACKGROUND OF THE INVENTION

1. Field of the Invention

The present invention relates to tissue sampling. More specifically, it relates to an apparatus and method for removing a sample of breast tissue for histo pathological examination. Even more specifically, it relates to an apparatus and method wherein a guiding spool is aligned over compressed breast tissue of a suspicious nature, the alignment is verified by the positioning of markings on the spool with those of the mammography apparatus, with the taking of an X-ray through the central aperture of the radiopaque spool to determine that the micro-calcification or lesion is located beneath, and with the advancement of a tube-like punch through the breast to remove the suspicious tissue for examination.

More generally, the invention relates to any type of alignment and sampling device wherein energy, which could be of various frequencies, is used to locate an anomalous area not immediately accessible, and where a bore or punch guide having an aperture therein that is transparent to the specified frequency is aligned over the anomalous area to confirm the accurate alignment and direct the punch to remove the area in question.

2. Description of the Prior Art

One of the most common forms of cancer is that of the female breast. Women are urged to examine themselves regularly for suspicious lumps or areas within the breast, and it is also recommended that a regular schedule of mammographic examination be maintained, especially above a certain age. In the case of non-palpable lesions or microcalcifications that are uncovered through these mammographies, it is necessary to obtain a sample of the suspicious tissue for histo pathological examination. This is done by various methods including surgical biopsy procedures and aspiration of the sample through needles. Both these methods have their drawbacks, however, in that the surgical procedure can entail a large initial incision, leaving a scar that can cause apprehension to the patient, and in the needle aspiration, that the microcalcification or lesion is still present in the breast, and that subsequent mammographies will reveal it, causing confusion, and the possibility of an unneeded, redundant second procedure. The present invention seeks to address these problems by providing a method and apparatus that substantially entirely removes the area in question while leaving a minimal amount of scarring. It secondly overcomes a disadvantage in the surgical procedures that require a guide wire placement in the breast and the subsequent moving of the patient to an operating theater for the actual excision of the tissue where, firstly, the guide wire can be dislodged from the correct position while the patient is transported and, secondly, the cost involved of providing and staffing the two separate locations or rooms in the medical facility. The present invention allows the practitioner to perform the procedure in one location, with the invasiveness thereof being kept to a minimum. In a search at the U.S. Patent and Trademark Office, a number of patents were uncovered that are deemed relevant to the instant invention:

In U.S. Pat. No. 5,197,482 issued on Mar. 30, 1993 to William R. Rank et al. there is disclosed a helical tipped lesion localization needle device and method. This constitutes a helically wound coil attached at both ends of a shaft, and is designed to be inserted into the body through a cannula. The helical construction allows the device to be rotated to advance the marker into the lesion for subsequent surgical procedures. In contrast to the present invention, the guide spool fastened to the outer portion of the patient is absent, as is the tubular hollow cutting punch of the present invention.

Next is U.S. Pat. No. 5,209,232 issued on May 11, 1993 to Simha Levene. This discloses a system of biopsy needle positioning wherein the position of the needle holder as it progresses into the patient's breast is monitored by a CPU such that images are provided to constantly update the progress of the biopsy needle towards the lesion. This is clearly different from the present invention in that no cutting punch is taught, the Levene patent being a positioning system for a needle prior to a surgical excision procedure.

In U.S. Pat. No. 5,056,523 issued on Oct. 15, 1991 to John E. Hotchkiss et al. there is disclosed a breast lesion localizer. This involves a first and second radiolucent platform that are in a movable, parallel, and spaced apart relationship to one another. The uppermost of these platforms contains an insert with a plurality of probe passages. Radiopaque scales are provided coplanar to the probe positioning guide to allow the operator to judge the depth of the lesion relative to the platforms and, thus, the probe guides. The probe can thus be inserted proximate the suspicious tissue and the tissue aspirated. Unlike the instant invention, there is no teaching of the guide spool, the aperture therein, nor of the tubular cutting member for the excision of the tissue.

U.S. Pat. No. 5,213,100 issued on May 25, 1993 to Herbert Summ discloses a mammography apparatus with a stereotactic biopsy unit. In this device, the holders for the biopsy needle extend parallel to the plane of exposure and have at their ends releasable closures that allow the patient to be moved away from the unit after the placement of the needles without disturbing the placement of the indicating needles. As in the patents discussed above, there is not seen the guide spool with its radiopaque aperture for alignment with the suspect tissue, nor is there seen the cutting punch of the present invention.

Lastly, U.S. Pat. No. 5,078,142 issued on Jan. 7, 1992 to Bernard W. Siczek et al. discloses a mammographic needle biopsy system. In this invention, the patient lies on a table which includes a breast aperture through which the breast pendulantly protrudes. A compression paddle presses the breast against an X-ray film holder and a needle holder that is adjustable through azimuth, elevation, and insertion depth is controlled through a computer to place the aspirating needle at the suspect area. Unlike the instant invention, there is no complete excision of the suspect area, nor is the guide spool required for the present invention taught.

None of the above inventions and patents, taken either singly or in combination, is seen to describe the instant invention as claimed.

SUMMARY OF THE INVENTION

Briefly, the present invention is an apparatus and method for obtaining samples of suspicious breast tissue. The breast is placed between two plates, which compress, and therefore stabilize the tissue. The upper compression plate has an aperture therein that allows for the placement of a guide spool having a flesh adhering surface thereon onto the compressed breast itself. Markings on the spool allow for accurate placement using the cross hairs, or laser pointer, of the mammographic unit. For additional placement verification, the guide spool is radiopaque and, thus, an X-ray taken directly down through the aperture will aid in ascertaining if the spool is properly placed. A tubular punch is advanced and rotated, cutting through the tissue, which is recovered in the tube. Alternatively, a localizing needle can be placed with its tip proximate the calcification, a guide wire mandrel having the same diameter as the guide spool aperture placed over it, the guide spool placed and aligned, the mandrel removed, and the tubular punch is inserted and advanced as above, removing the tissue in question, along with the localizing needle.

Accordingly, it is a principal object of the invention to provide an improved breast biopsy apparatus and method of use that will overcome the disadvantages of the prior art in a simple and effective manner.

It is another object of the invention to provide a breast biopsy apparatus that allows the sample of breast tissue to be taken at one location, without the intermediate step of moving the patient from the mammography apparatus to an operating room.

It is a further object of the invention to provide a breast biopsy apparatus and method that completely excises the tissue in question so as to eliminate the possibility of a redundant and wasteful procedure if the lesion or microcalcification is detected in a subsequent mammography.

Still another object of the invention is to provide a breast biopsy apparatus and method that allows for a guide spool for the cutting tube or punch to be placed by providing markings on the spool for alignment with the cross hairs, or laser pointer, on the mammography equipment.

Still yet another object of the invention is to provide a breast biopsy apparatus and method that includes an aperture in the radiopaque guide spool for both guiding the cutting tube or punch and also aids in alignment by allowing an X-ray to be taken "down" through the aperture such that, if the lesion or suspicious area is seen therein, confirms that the spool is accurately placed.

It is yet another object of the invention to provide a breast biopsy apparatus and method that removes the lesion or calcified area with less invasiveness than current surgical biopsy procedures.

It is yet still another object of the invention to provide a method which recovers adequate tissue for histo pathologic diagnosis.

Finally, it is a general goal of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

The present invention meets or exceeds all the above objects and goals. Upon further study of the specification and appended claims, further objects and advantages of this invention will become apparent to those skilled in the art.

Finally, it is a general goal of the invention to provide improved elements and arrangements thereof in an apparatus for the purposes described which is inexpensive, dependable and fully effective in accomplishing its intended purposes.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is partial perspective view of the present invention showing the guide spool in place on the breast through the opening in the upper compression plate.

FIG. 2 is a perspective view of the guide spool, showing its lower surface with the tacky adhesive for facilitating firm contact with the patient's breast.

FIG. 3 is a partially cutaway side view of the guide spool and the cutting tube or punch.

FIGS. 8A–8G and FIGS. 8I–8K is a cutaway side view showing various steps in the alternative embodiment of the invention, wherein a localizing needle is placed to assist in the guiding of the cutting punch.

DETAILED DESCRIPTION OF THE PREFERRED EMBODIMENTS

Figure 6:
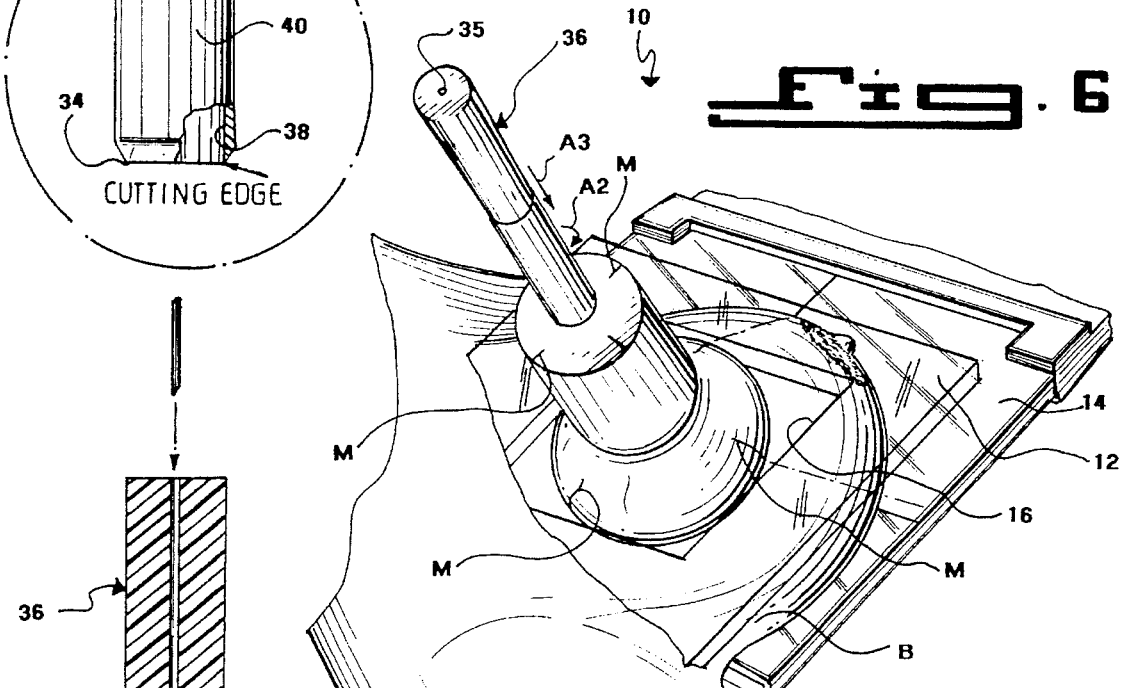
FIG. 6 is a perspective view of the guide spool in place on the patient's breast, with the cutting tube or punch being advanced into the guide spool aperture.

Referring to FIGS. 1 and 6, the present invention is indicated generally at 10. The breast B of the patient P is placed between two compression plates 12, 14. These plates are in a spaced apart relationship to one another and are adjustable such that breast B can be compressed; that is the tissue thereof can be held such that it will not move inadvertently while the biopsy procedure is being carried out. The top plate 12 has an access opening 16 located proximate its center. This access opening is dimensioned such that the guide spool 20, which will be discussed more fully below, can be placed therein, in contact with the surface of the breast B. The compression plates 12, 14 are known in the mammographic art, and apart from the aperture 16 in the top plate 12, would be similar to the known art devices, being preferably made from a radiolucent material so as not to interfere with the mammographic procedure.

Prior to the usage of the instant invention, it is to be assumed that a suspicious area has been found in the breast B of the patient P. The microcalcified areas or lesions that the present invention concerns itself with are primarily non-palpable. Thus the location of the lesion in the breast B is known before the present invention is called into use.

The discussion now turns to the guide spool 20. The spool 20, in the preferred embodiment described herein has an asymptotic shape: i.e. a bell shape (best seen in FIG. 2), and includes an outer wall 22, a bottom surface 24, and a top surface 26. Extending completely from the top surface 26 to the bottom 24 is a guide aperture 28. The bottom surface 24 is covered with a tacky adhesive 29. This adhesive serves to prevent the spool 20 from moving during the procedure. The spool 20 also includes guide markings M, as seen in FIG. 6. These guide markings M allow the user to align the spool 20 on to the surface of the breast by corresponding to the alignment crosshairs on the mammographic device. The markings M are located on the top surface 26 of the spool 20, and also proximate the bottom surface 24 on the outer wall. The spool 20 is preferably made from a radiopaque material, since guide aperture 28 also serves as a supplementary alignment means in that if, after the guide spool 20 is in place, the user were to expose an X-ray from directly above the guide spool 20 in the direction indicated by arrow A1 in FIG. 1, the presence of the calcified area in the developed plate would indicate that the spool 20 will guide cutting tube or punch 30 correctly, as will be hereinafter described.

Figure 4:
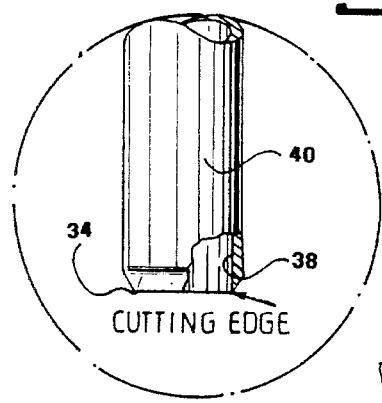
FIG. 4 is an expanded partial cutaway view of the indicated area in FIG. 3 showing the beveled cutting edge of the punch.
Figure 5:
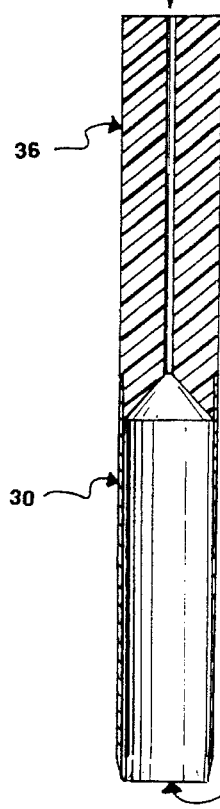
FIG. 5 is a cutaway side view of the localizer needle mandrel used in the alternative embodiment of the invention.

Turning now to FIGS. 3, 4, and 5, the construction and disposition of the cutting tube or punch 30 will be discussed. The tube 30 has an open end 32 that is surrounded by a beveled cutting edge 34 (best seen in FIG. 4). At the distal end of the tube from the cutting edge 34 is a handle 36. The cutting tube 30 thus includes an inner wall 38 and an outer wall 40. The cutting portion of the tube 30 would preferably be made of a surgical grade of stainless steel or some other biologically neutral substance that has the ability to be sterilized after use, if the user should so desire.

Figure 7:
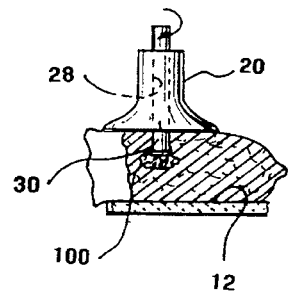
FIG. 7 is a partially cutaway side view showing the cutting punch advancing into the breast tissue and approaching the calcified area.

For the operation of the present invention, the breast B is compressed between compression plates 12, 14, as can be seen in FIG. 1. Using either the, laser light pointer, cross hairs on the mammographic system and the corresponding markings M on the guide spool 20, the "bore sighting" technique through the guide aperture 28 of the guide spool 20 discussed above, or a combination of all, the guide spool 20 is placed such that the guide aperture lies directly in a line with the calcified area in the breast tissue B. The cutting tube 30 is then placed within the guide spool aperture 28 and is advanced while being rotated, as indicated by directional arrows A2 and A3 in FIG. 6, to cut into the breast tissue and excise the portion desired for examination. In FIG. 7 there is shown an example of the cutting tube 30 advancing towards a calcified area 100 in the breast tissue B. It is contemplated that the cutting tube 30 could be advanced completely through the breast tissue, until it comes into contact with compression plate 12, and then removed. The size of the cutting tube 30 would be from to 1 centimeter in diameter though other dimensions, of course, could be used, depending on the size of the lesion and the experience, guided by wisdom, of the practitioner.

The discussion now is directed to FIGS. 8A–8G and 8I–8K where, in an alternative embodiment of the invention, a guide wire W is initially placed within the breast tissue to mark the calcified area 100. A guide wire mandrel 50 is placed over the wire W, as seen in FIG. 8B, and moved in the direction indicated by the arrow A4 until it comes into contact with the breast B. The mandrel 50 is dimensioned identically to that of the cutting tube 30 so that it fits smoothly into the guide aperture 28 of the spool 20. Thus, the spool 20 can be placed over the guide wire mandrel 50, by inserting mandrel 50 into the aperture 28. As seen in FIGS. 8C and 8D, the spool 20 is brought into contact with the breast B and the tacky adhesive surface 29 on the bottom 24 of the spool 20 adheres to the breast B. The guide aperture 28 is now aligned with the calcified area 100 and the mandrel 50 can be removed from the aperture 28. Cutting tube or punch 30 is now placed in the guide aperture 28 and is advanced through the breast B, as can be seen in FIGS. 8E, 8F, 8G, and 8K, with 8K showing the cutting tube extending completely through the tissue and touching the compression plate 14. FIGS. 8I and 8J show the removal of tissue sample within the cutting tube 30, along with the guide wire W. Following hereinafter is a list of the elements designated by reference numbers in the above specification:

| | |
|---|---|
| biopsy apparatus | 10 |
| upper compression plate | 12 |
| lower compression plate | 14 |
| breast | B |
| top plate access opening | 16 |
| guide spool | 20 |
| patient | P |
| spool outer wall | 22 |
| spool bottom surface | 24 |
| spool top surface | 26 |
| spool guide aperture | 28 |
| tacky adhesive | 29 |
| spool guide markings | M |
| directional arrow | A1 |
| directional arrow | A2 |
| directional arrow | A3 |
| directional arrow | A4 |
| cutting tube or punch | 30 |
| open end | 32 |
| beveled cutting edge | 34 |
| central aperture for alignment with guide wire or laser light pointer | 35 |
| handle | 36 |
| inner wall | 38 |
| outer wall | 40 |
| calcified area or lesion | 100 |
| guide wire | W |
| guide wire mandrel | 50 |

It is to be understood that the present invention is not limited to the sole embodiment described above, but encompasses any and all embodiments within the scope of the following claims.

I claim:

1. An apparatus for the excision of prelocated, specific tissue located in a bodily protuberance comprising:

means for immobilizing the protuberance, said means to immobilize the protuberance comprising a first and a second compression paddle, said first and second paddles being in an adjustable, spaced apart relationship in respect to one another, and said first and second paddle are parallel to one another, an access opening being included in one of said compression paddles, said access opening dimensioned such that said positioning means can be placed therein, said positioning means thus being in contact with the protuberance;

a hollow cutting tube having a cylindrical interior and an open end, said open end defining a beveled cutting edge;

positioning means for the positioning of said hollow cutting tube such that said hollow cylindrical interior of said cutting tube is coplanar with the specific tissue to be excised, said positioning means including an aperture therethrough, said aperture dimensioned to smoothly receive said cutting tube; and rotation and advancement means for rotating and advancing said hollow cutting tube through said positioning means aperture and into the protuberance such that the specific tissue is contained within said hollow interior of said cutting tube when said tube is removed from the protuberance.

2. The apparatus according to claim 1, wherein said positioning means includes a top surface and a bottom surface, with said positioning aperture extending from said top surface to said bottom surface, and where said bottom surface is in contact with the protuberance.

3. The apparatus according to claim 2, wherein said bottom surface includes a tacky adhering means for the prevention of inadvertent movement after said positioning means is placed in contact with the protuberance.

\* \* \* \* \*